(12) United States Patent
Lundgren

(10) Patent No.: US 6,227,858 B1
(45) Date of Patent: May 8, 2001

(54) BONE ANCHORING ELEMENT

(75) Inventor: Dan Lundgren, Hovas (SE)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/367,999

(22) PCT Filed: Feb. 25, 1997

(86) PCT No.: PCT/SE97/00314

§ 371 Date: Aug. 24, 1999

§ 102(e) Date: Aug. 24, 1999

(87) PCT Pub. No.: WO98/36701

PCT Pub. Date: Aug. 27, 1998

(51) Int. Cl.[7] .................................................. A61C 8/00
(52) U.S. Cl. ................................................. 433/173; 433/174
(58) Field of Search .............................. 433/173, 174, 433/175

(56) References Cited

U.S. PATENT DOCUMENTS

| | | | |
|---|---|---|---|
| 3,849,887 | 11/1974 | Brainin | 433/173 |
| 4,790,753 | * 12/1988 | Fradera | 433/174 |
| 5,362,236 | * 11/1994 | Branemark | 433/173 |
| 5,372,503 | * 12/1994 | Elia | 433/215 |
| 5,417,570 | * 5/1995 | Zuest et al. | 433/177 |
| 5,727,942 | * 3/1998 | Hartmann et al. | 433/173 |

FOREIGN PATENT DOCUMENTS

WO 91/14404 * 10/1991 (SE).
9114404 10/1991 (SE).

* cited by examiner

*Primary Examiner*—John J. Wilson
*Assistant Examiner*—Melba Bumgarner
(74) *Attorney, Agent, or Firm*—James Ray & Associates

(57) ABSTRACT

A bone implant for implantation into a bone tissue and for the connection of a prosthetic structure thereto, the bone implant including a screw-threaded portion for insertion into the bone tissue, a neck portion extending along an axis from the screw-threaded portion, the neck portion terminating in an end surface, the end surface being provided with a threaded blind hole for attachment of the prosthetic structure to the bone implant, a cover element, and an attachment mechanism for attaching the cover element to the neck portion of the bone implant, the cover element including a cupola-shaped outer surface and the cover element having a thickness extending inward from the cupola-shaped outer surface for a substantial distance along the axis of the neck portion when the cover element is attached to the neck portion by the attachment mechanism.

20 Claims, 5 Drawing Sheets

BONE ANCHORING ELEMENT

FIELD OF THE INVENTION

The invention relates to a direct connected bone anchoring element for prosthetic structures, including an implant to be inserted into bone tissue, the end surface of the implant (which is the outer end surface of the implant in the implanted position thereof) being arranged for attachment of a prosthetic structure thereto.

BACKGROUND OF THE INVENTION

It is known in the prior art to anchor permanently (e.g., dental prostheses or crown and bridge structures) to anchoring elements integrated into the bone (i.e., implants) through the use of extension pieces or spacers which penetrate through the mucous membrane. Such implants are most often cylindrical and screw-shaped. These implants are inserted by a separate surgical operation and are completely covered by the mucous membrane. After a minimum critical ingrowth period, a further surgical operation is effected in order to connect the implants to the actual prosthetic structure through such extension pieces of suitable length. This so called "two-step method" is utilized in order to reduce the failure frequency, which is considered too high in a one-step method. In the one-step method, the implant penetrates the mucous membrane covering the bone during the installation of the implant. The higher failure frequency in the one-step method is due to the load transferred to the sensitive interface between bone tissue and implant via the portion of the implant which is already positioned in the oral cavity above the mucous membrane during the initial period of the ingrowth phase. In addition, there is the risk of an infection in the interface between the implant and the soft tissue easily propagating along the implant wall and degrading the bone tissue before ingrowth has taken place.

However, recently controlled studies have been conducted in which good results with the one-step technique have been demonstrated, provided that the portion of the implant penetrating the mucous membrane does not project to too great of a degree beyond the surface of the mucous membrane where it will be exposed to too great of loading forces, and provided also that this portion of the implant is kept completely free from microorganisms continuously, so that infection (with accompanying destruction of the tissue) will not arise.

Provided that these conditions are satisfied, it is thus very likely that the one-step technique (also in a large scale) will provide as good of results as the two-step technique. This means that both techniques will be applied within their respective indication fields.

In the two-step method, the implant is positioned in the bone tissue such that the most superficial portion thereof will be at the same level as, or slightly above, the bone surface where ingrowth is allowed to take place. The implant becomes covered by soft tissue and remains unloaded for a period which is sufficiently long that the implant becomes intimately anchored (e.g.,"gets firmly rooted") in the surrounding bone tissue. A second surgical operation is then performed, in order to uncover the implant by punching an aperture through the covering mucous membrane (or by cutting through the membrane) and in order to connect extension pieces to the implant.

One purpose of the present invention is to provide a more rational and less expensive method, which results in an improved ingrowth into the most superficial portion of the bone and the periosteal and connective tissue located on the bone surface.

To this purpose, a bone anchoring element according to the invention is described in the appended claims.

Contrary to prior art types of implant intended for the two-step method, the implant described herein can be completely covered by the mucous membrane and can, nevertheless, be uncovered, without applying extension elements. This provides several advantages:

Reduction of costs and simplification of the manufacture through the elimination of the spacer screw (and spacer socket).

The implant is suitable for use in the one-step technique, as well as in the two-step technique.

The diameter of the implant can be considerably reduced, without increased risk of fracture, due to the fact that the blind hole for the fastening screw has a considerably smaller diameter than the hole for a spacer screw. This increases the indication domain considerably as far as jaws having a small buccolingual width are concerned.

Edge cutting with accompanying destructive bone cutting is eliminated.

Allows for a simplified secondary operation with the two-step technique, since the covering element of the implant can easily be palpated, and since the neck of the implant is easily available for direct connection to the prosthetic structure. An X-ray check, in order to certify correct connection between implant components, is eliminated, and complicating bone overgrowth is precluded.

There is no need of turning up a larger flap. This increases the patient comfort, spares the jaw bone and makes the surgery simpler.

The joint between the implant and the spacer is eliminated. This eliminates annoying odor, if any, and infection involving risk of bone destruction, in case the joint is located adjacent the bone edge.

Optimal aesthetics, by elimination of the spacer, and by the fact that the end surface of the implant, in particularly delicate cases, can be beveled (towards the buccal side).

The thickness of the soft tissue can be controlled during ingrowth by the shape of the covering element being controlled.

Considerably smaller critical height of the prosthetic structure, by connection thereof directly to the implant, which facilitates the prosthetics and increases the indication domain.

Minimal risk of buccal screw apertures through angled passages.

Preferably, the implant is made of a material which has a sufficient degree of biocompatibility and strength in order to be permanently implanted as an anchoring element for prostheses, crowns, or bridges. It can consist of ceramics, metal, or tissue tolerant plastics, or combinations thereof. An example of a suitable metal is pure titanium, which is prepared so that the surface thereof is completely free from organic material and which is preferably given a suitable surface roughness by turning, blasting, or by another suitable preparation technique. The implant can also be coated on the surface thereof with a material which optimizes the ingrowth of the implant to form a highly intimate connection with the surrounding bone. For example, titanium can be applied to the implant by so called plasma spraying, or hydroxyl apatite. Preferably, the implant is screw-shaped.

BRIEF DESCRIPTION OF THE DRAWINGS

The invention will now be described in more detail, with reference to the accompanying drawings, in which.

DETAILED DESCRIPTION OF THE PREFERRED EMBODIMENTS

Figure 1:
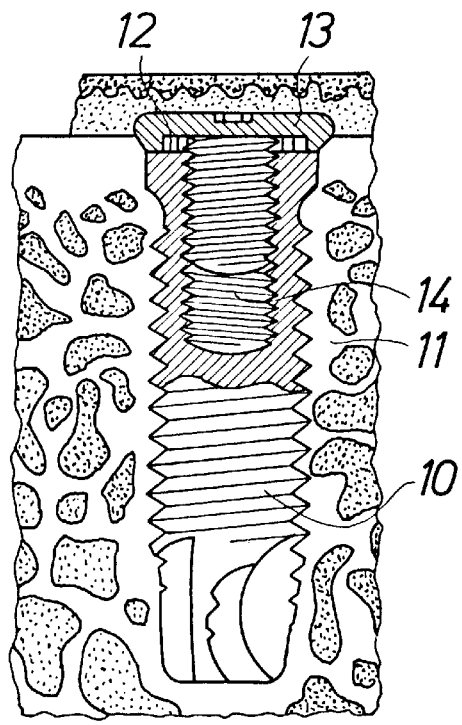
FIG. 1 is an elevational cross-sectional view of a prior art screw implant which, at present, is most commonly appearing on the market.

The prior art implant shown in FIG. 1 includes a screw which is made of or coated with titanium or another biocompatible material. It has a screw-threaded portion 10 which is screwed into a hole which has been drilled in the bone 11, such that the end surface 12 thereof will be located substantially at the same level as the surface of the bone 11. The implant has a hexagonal portion on the end surface 12, in order that a tool can be engaged therewith when the implant is to be screwed into the bone 11. The implant also has a threaded blind hole 14 for the attachment of an extension piece or spacer when the two-step method described above is employed. In FIG. 1, the implant is provided with a cover screw 13, which is screwed into the threaded blind hole 14.

Figure 2:
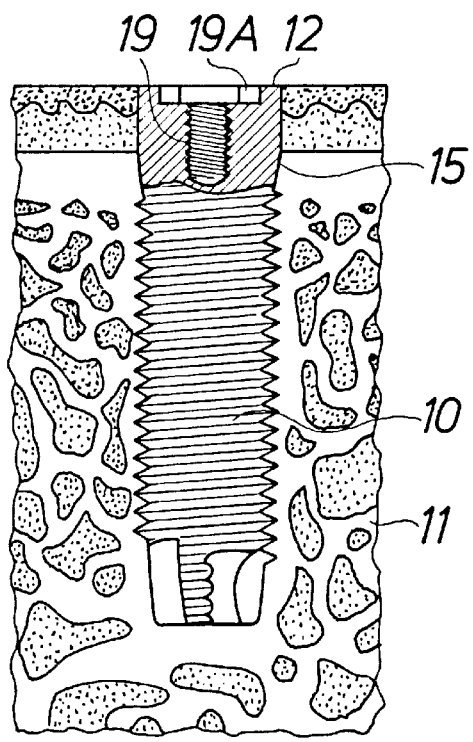
FIG. 2 is an elevational cross-sectional view of an implant constructed according to the invention.

The implant according to the invention, which is shown in FIG. 2, has a screw threaded portion 10 and a cylindrical neck portion 15, which has preferably been made smooth by turning and which may be polished. The neck portion 15 can have a length which is from 1 to 10 mm but which, preferably, is from 1 to 3 mm. The curved surface of the neck portion 15, at the transition from the threaded portion of the implant, is flush with the crests of the threaded portion, but preferably diverges slightly towards the end surface 12 of the implant. By this arrangement, there is provided a tight connection to the adjacent bone edges when the implant is being screwed into the bone, without detrimental overpressure being created in the bone tissue. At the same time, a sufficient screwing resistance is obtained, in order to impart stability to the implant.

The diameter of the implant can vary from some tenths of a millimeter and upwards but, in oral prosthetical function, preferably ranges from 2.0 mm to 8.0 mm. Preferably, the implant is made self-tapping.

Figure 7:
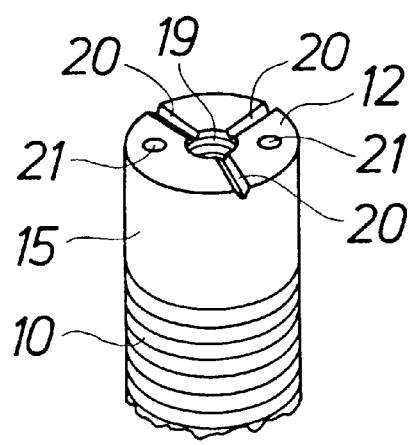
FIG. 7 is a fragmentary perspective view of an end surface of the implant according to another embodiment of the invention.

In the center of the upper end surface of the implant, there is provided a threaded axial blind hole 19, the diameter of which can vary in dependence on the dimension of the fastening screw which is used to retain the prosthetic structure, and in dependence on the diameter of the implant. At the upper end of the blind hole 19, there is provided an internal hexagonal portion 19A for engagement with a tool, by means of which the implant is screwed into the bone. The end surface 12 can also be provided with supplementary means for locking the prosthetic structure attached to the end surface against rotation. Such supplementary rotational locking means can include one or more grooves 20 or blind holes 21 (as shown in FIG. 7), and corresponding ridges or cylindrical or conical projections may be provided on the prosthetic structure to be attached to the end surface of the implant for engagement therewith. The supplementary rotational locking can also be provided by means of a raised or countersunk portion around the fastening screw with four or more walls to which a corresponding patrix or matrix attached to the corresponding prosthetic structure is exactly fitted.

Figure 3:
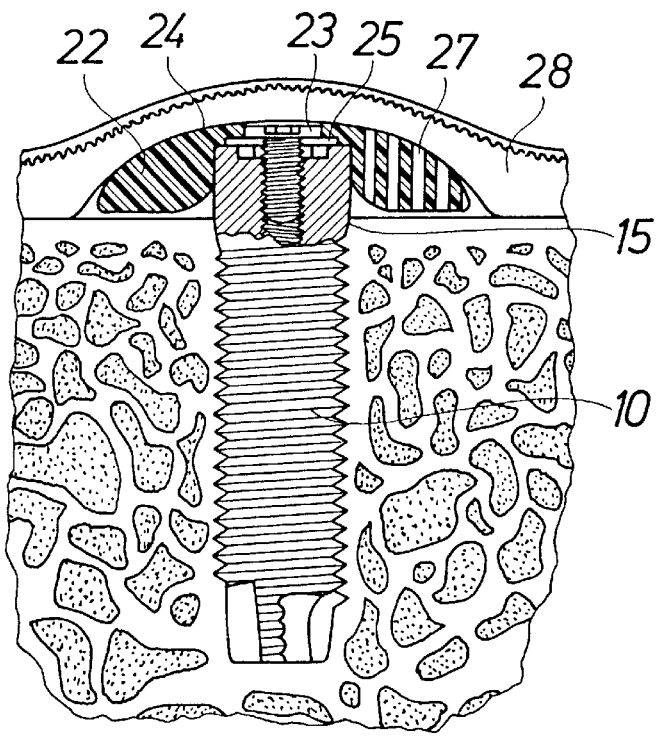
FIG. 3 is an elevational cross-sectional view of an implant constructed according to the invention and provided with a cover element.

Due to a well adjusted neck length, the implant can be implanted with covering mucous membrane and can integrate unloaded and without infectious contamination via the oral cavity, while the implant, by selection of correct neck length in relation to the thickness of the mucous membrane, can be easily palpated and uncovered by punching or in another manner, but in order to avoid the existing relatively great risk of perforation of the mucous membrane, there is preferably mounted to the inventive implant a cover element 22 shown in FIG. 3), which is attached by means of a screw 23 engaging the threaded hole 19 which is provided for receiving the fastening screw of the prosthetic structure. This cover element 22 has a gently rounded cupola shaped upper surface 24 and includes a body of a tissue tolerant and at least partially plastic material, which is attached to the head of the screw 23. The screw 23 and the head thereof can consist of titanium. The head engages the end surface 12 of the implant, a washer 25 being located therebetween. The tissue tolerant plastics can include a non-resorbable or, alternatively, a partly or completely resorbable polymer. The cover element 22 can be perforated in the portion thereof which is located outside the end surface of the implant. These perforations partially shown at 27, are preferably of a size which allows the formation of new tissue, which contributes both to the nutrition of the mucous membrane and the ingrowth process in the bone tissue adjacent the neck portion of the implant. The plastics (polymer) should have a consistence which is close to the consistence of the connective tissue, in order that the risk of perforation of the mucous membrane within 3 to 6 months after implantation shall be prevented. It should also be so plastic, at least at the periphery thereof, that it can be deformed without elastic return and without cracking or fracturing. It should also be possible to reshape—reduce—the plastics by means of a pair of scissors or with a scalpel.

FIG. 3 discloses how the implant and the cover element thereof is covered by connective tissue 28. When the implant has been anchored in the bone by ingrowth for 3 to 6 months after the implantation, the mucous membrane may be perforated by a cut or a circular aperture in order to uncover the neck portion 15 of the implant. In order to facilitate the identification of the implant when punching through the mucous membrane, the upper end surface of the cover element can include an aperture or a depression which can be palpated by means of a sond or the like. Uncovering of the cover element by punching causes the smallest possible damage of the tissue and thus the best possible healing within the shortest possible time in the important "sealing region" around the portion of the implant which penetrates the soft tissue.

Figure 4:
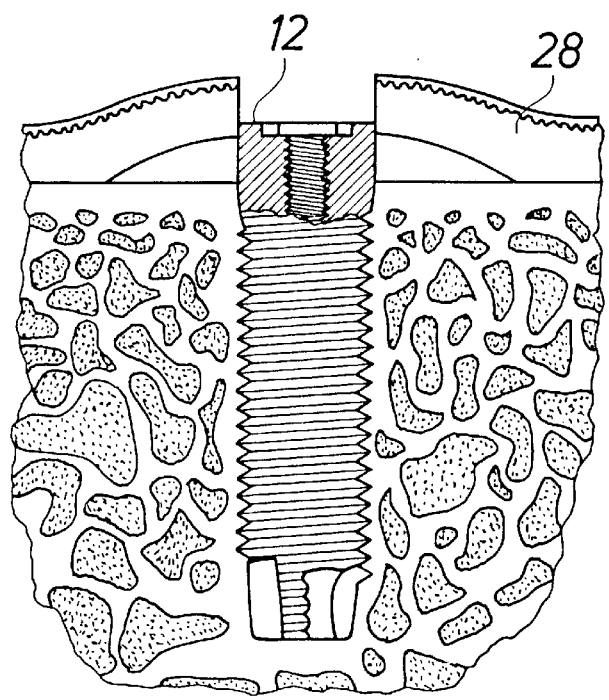
FIG. 4 is elevational cross-sectional view of the inventive implant shown in FIG. 3, after an aperture has been punched in the covering soft tissue and the cover element has been removed.
Figure 5:
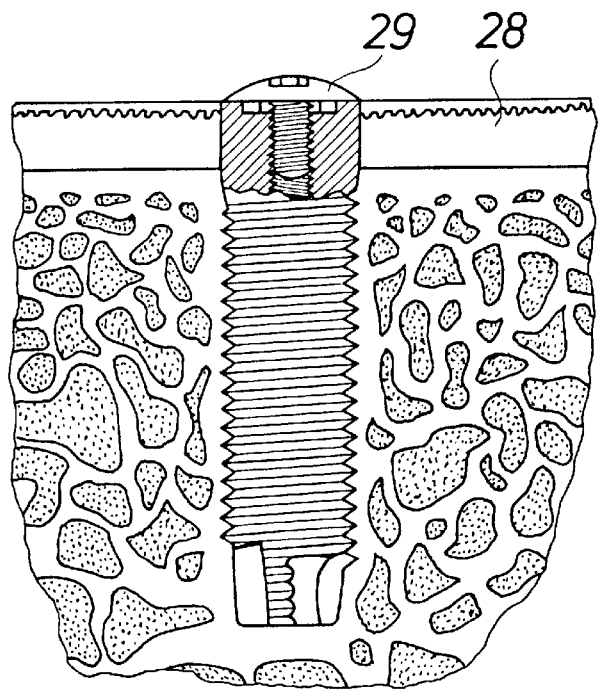
FIG. 5 is a elevational cross-sectional view of the inventive implant of FIG. 3, after the soft tissue has been laid down around the neck of the implant.

When the mucous membrane has been perforated and the cover element has been removed (see FIG. 4), the soft tissue is laid down and takes the place of that part of the cover element which surrounded the neck portion 15 of the implant, as is seen in FIG. 5, where a cover screw 29 of metal or plastics has been attached to the implant.

The described embodiment of the implant means that the spacer screw, which is a necessary element in the two-step systems available on the market, will be superfluous. As a consequence thereof, the implant system according to the invention is substantially rationalized and made less expensive. Moreover, the manufacture of the implant is simplified, due to the fact that no threaded central hole for a spacer screw in the threaded portion of the implant will be necessary. This means also that the strength of the implant will be increased and that the implant can be given a smaller diameter, which in turn means that the implant can be inserted by surgery in regions having a smaller bone width than that required by implants available so far.

Another decisive advantage is that the connective joint provided between the implant and the spacer at the level of the bone surface of two-step implants available on the market now will be eliminated. This provides obvious advantages for optimal ingrowth in this sensitive border zone region. The only joint which is provided is the connection joint between the implant and the prosthetic structure, which also exists in other systems. This joint here will be located at a distance of at least 1–2 mm from the bone surface, preferably substantially at the same level as the surface of the mucous membrane.

This means that the risks of complications due to growth of microorganisms or penetration of products produced by microorganisms or other exciting substances with inflammation or tissue destruction as a consequence thereof will be completely eliminated. Moreover, the construction of the implant described above, having a suitably adjusted implant neck, means that surgical uncovering by punching does not necessarily include tissue trauma at the transition between bone surface and connective tissue. A still further advantage is that the cover element secures separation of the connective tissue (which, closest to the implant, is located above the cover element) from the bone tissue, which is located under the cover element. This would include less risk of connective tissue growing down along the neck of the implant at temporary bone resorption, if any, in this region due to the surgery.

The cover element is shaped such that it has a specific thickness at the center and, at the same time, surrounds the neck portion of the cylindrical implant from the end surface to about 0.5 to 1 mm above the bone surface, the cover element thus occupying the soft tissue height corresponding substantially to the thickness of the mucous membrane. When the implant has been uncovered by punching and the cover element has been removed, the adjacent soft tissue will occupy the space occupied by the portion of the cover element that surrounded the upper part of the implant. As a consequence thereof, the uncovered implant will automatically extend to the level of the surface of the mucous membrane or slightly below or above this surface depending on how one has intentionally planned in the specific case [See, e.g., FIG. 5.]

Figure 6:
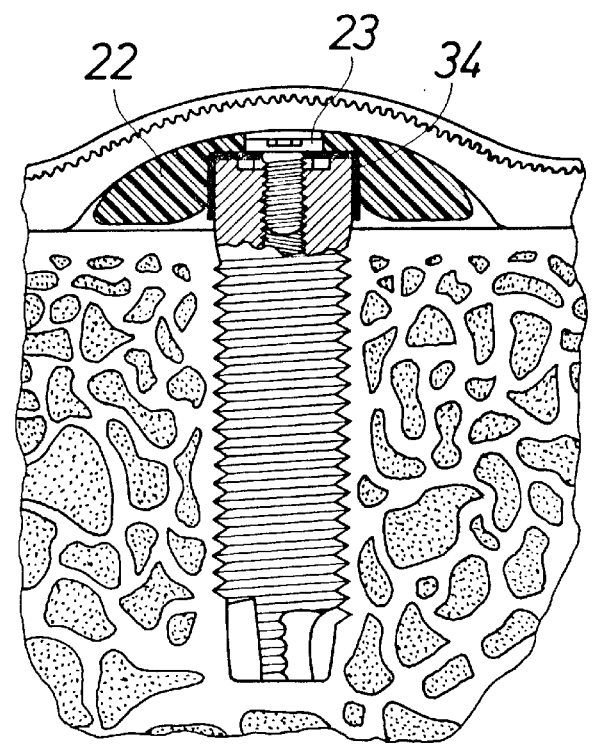
FIG. 6 is an elevational cross-sectional view of the inventive implant provided with a cover element according to another embodiment of the invention.

Another embodiment of the cover element 22 is shown in FIG. 6, wherein the central portion with the screw 23 surrounds the implant neck as a cap 34, which occupies the height of the neck substantially corresponding to the thickness of the mucous membrane. Above and outside the cap 34, the plastic body of the cover element 22 is located, which body is constructed preferably of plastics. This latter material can be applied separately in relation to the central cap.

In the embodiment of FIG. 6, the cap 34 can form an annular bead or projections on the inside surface thereof to engage an annular groove or depressions on the outside surface of the neck portion 15, for attachment of the cover element 22 to the implant. In such case, the central fastening screw 23 can be dispensed with.

The neck portion 15 can be shaped to be so conical (i.e., diverging towards the end surface of the implant) that the end surface 12 of the implant has a diameter which is substantially larger than the diameter of the rest of the implant, in order that the neck portion 15 shall harmonize with the overlaying prosthetic structure and in order that a sufficiently dimensioned fastening screw can be used for attaching the prosthetic structure, due to the fact that the threaded hole 19 can be made larger.

Figure 8:
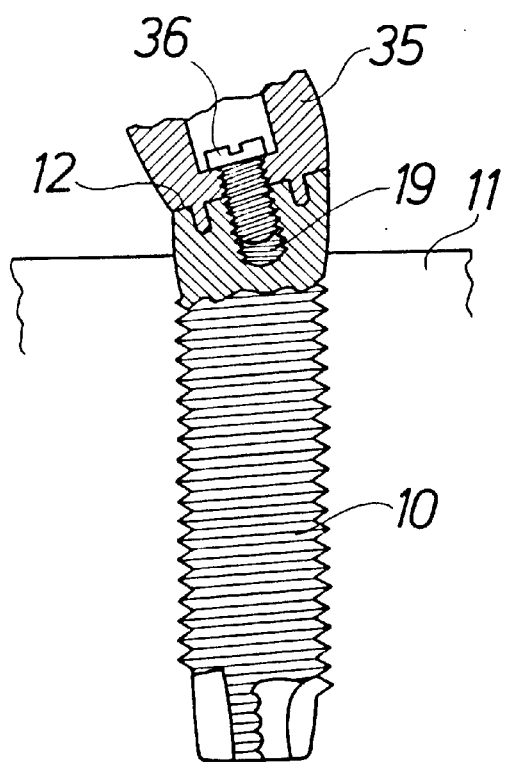
FIGS. 8 to 11 are views illustrating different embodiments of the connection surface of the implant according to the invention.

In the embodiment of the implant according to the invention which is shown in FIG. 8, the end surface 12 is beveled at an angle ranging from 5° to 45°. The threaded central hole 19 in the end surface 12 is perpendicular to the end surface 12. This allows the inventive implant having an angled end surface to be installed at an inclination where the actual bone mass is utilized in the best manner, for a longest lasting implant, the angled end surface at the same time optimizing the possibilities of attaching the prosthetic structure, fragmentarily shown at 35. Additionally, the direction of the fastening screw 36 can be adjusted optimally to the bite conditions. In cases where the implant is of the screw-type, i.e. provided with threads, particularly the self-tapping implants allow for some degree of tolerance, which means that the implant can be tightened to a level which is in agreement with the desired direction of the beveled end surface. This is particularly true if the implant has a small thread pitch. The beveled oval end surface can be shorted in regions where the radius thereof is larger, in order to harmonize with a circular end surface in the prosthetic structure.

Figure 9:
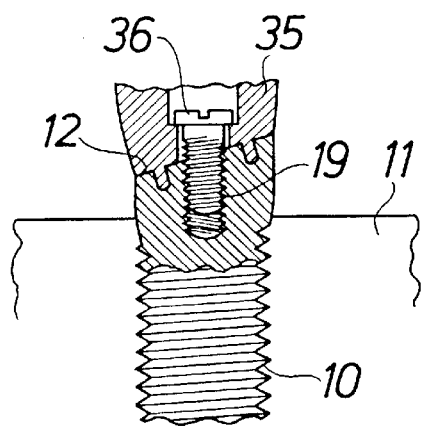

In a further embodiment shown in FIG. 9, the beveled end surface 12 faces buccally, for aesthetic optimization by the joint between the prosthetic structure 35 and the implant being located at a sufficiently low level in relation to the buccal soft tissue surface, the joint for the rest not being located too low. A shape exactly fitting the beveled end surface is imparted to the prosthetic structure.

Figure 10:
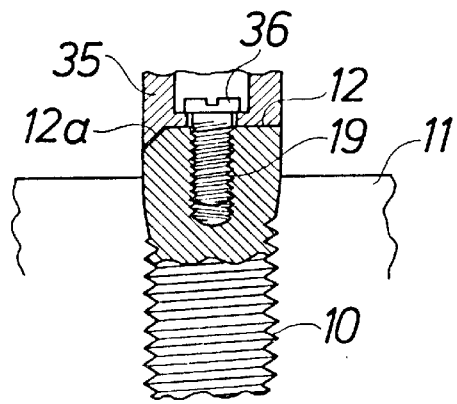
Figure 11:
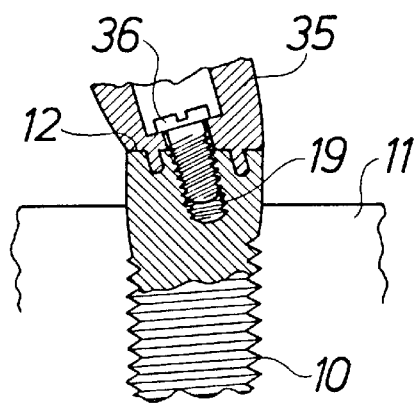

In FIG. 10 there is shown an embodiment wherein the beveled surface forms only a minor part 12a of the end surface 12, in the basic embodiment described, and thus does not include that part of this surface which is occupied by the fastening screw 36. The prosthetic structure 35, in this case, is also given a shape fitting exactly the end surface 12.

In a further embodiment shown in FIG, 11, the end surface 12, as in the basic embodiment, is perpendicular to the longitudinal axis of the implant, but the central hole is angled between 5° and 45°. At the same time, the surface of the structure 35 to be attached against the end surface 12 of the implant is angled at an angle corresponding to that of the central hole 19. By this arrangement, the same effect is achieved as in the embodiment presented above, wherein it was the intention to utilize the bone mass for the best possible retention by providing an angle between the implant and the prosthetic structure, the prosthetic structure, at the same time, being optimally adjusted to the bite conditions.

The invention has been described with regard to bone anchoring elements intended to be located substantially in Saw bones for anchoring a prosthesis or bridge structure. However, the invention is not limited to this particular field; it can be applied also in other connections where a bone anchoring is required.

What is claimed is:

1. A bone implant for implantation into a bone tissue and for the connection of a prosthetic structure thereto, said bone implant comprising:
   a screw-threaded portion for insertion into such bone tissue;
   a neck portion extending along an axis from said screw-threaded portion;
   said neck portion terminating in an end surface;
   said end surface being provided with a threaded blind hole for attachment of such prosthetic structure to said bone implant;
   a cover element; and
   an attachment mechanism for attaching said cover element to said neck portion of said bone implant;
   said cover element including:
      a cupola-shaped outer surface having an exterior periphery; and
      a thickness of said cover element that increases from said exterior periphery extending radially inward for a predetermined distance along said neck portion when said cover element is attached to said neck portion by said attachment mechanism.

2. A bone implant according to claim 1, wherein:
   said screw-threaded portion extends, along a substantially central axis; and
   said end surface is disposed at a substantially non-orthogonal angle with respect to said substantially central axis of said screw-threaded portion.

3. A bone implant according to claim 1, wherein said end surface includes at least one of
   a beveled segment; and
   a recessed segment.

4. A bone implant according to claim 1, wherein:
   said threaded blind hole is disposed at an angle with respect to said substantially central axis of said screw-threaded portion.

5. A bone implant according to claim 4, wherein said angle is substantially within a range of between about 10° to about 30°.

6. A bone implant according to claim 1, wherein:
   said cover element additionally includes a cap portion detachably connected to said bone implant, said cap portion substantially covering said end surface and said cap portion substantially surrounding said neck portion.

7. A bone implant according to claim 6, wherein said bone implant additionally includes:
   a projection provided on at least one of said cap portion and said neck portion; and
   a recess provided on the other of said cap portion and said neck portion;
   said projection and said recess being dimensioned to releasably engage one another when said cap portion substantially surrounds said neck portion.

8. A bone implant according to claim 1, wherein:
   said cover element comprises at least one of a non-resorbable plastic, a silicone, a metal, and titanium.

9. A bone implant according to claim 1, wherein said cover element includes perforations extending therethrough.

10. A bone implant according to claim 1, wherein said cover element is substantially deformable.

11. A bone implant for implantation into a bone tissue and for the connection of a prosthetic structure thereto, said bone implant comprising:
    a screw-threaded portion for insertion into such bone tissue;
    a neck portion extending along an axis from said screw-threaded portion;
    said neck portion terminating in an end surface;
    said end surface being provided with a threaded blind hole for attachment of such prosthetic structure to said bone implant;
    a cover element; and
    an attachment mechanism for attaching said cover element to said neck portion of said bone implant;
    said cover element having an exterior periphery, a cupola-shaped outer surface, and an inner surface; substantially adjacent such bone tissue when said bone implant is implanted into such bone tissue and said cover element is attached to said neck portion of said bone implant;
    said inner surface extends at a substantially orthogonal angle with respect to said axis of said neck portion from said exterior periphery toward said neck portion a predetermined distance when said cover element is attached to said neck portion; so that when said bone implant is implanted into such bone tissue, said inner surface is disposed substantially adjacent such bone tissue extending radially inward from said exterior periphery for a predetermined distance toward said axis.

12. A bone implant according to claim 11, wherein:
    said screw-threaded portion extends along a substantially central axis; and
    said end surface is disposed at a substantially non-orthogonal angle with respect to said substantially central axis of said screw-threaded portion.

13. A bone implant according to claim 11, wherein said end surface includes at least one of
    a beveled segment; and
    a recessed segment.

14. A bone implant according to claim 11, wherein:
    said threaded blind hole is disposed at an angle with respect to said substantially central axis of said screw-threaded portion.

15. A bone implant according to claim 14, wherein said angle is substantially within a range of between about 10° to about 30°.

16. A bone implant according to claim 11, wherein:
    said cover element additionally includes a cap portion detachably connected to said bone implant, said cap portion substantially covering said end surface and said cap portion substantially surrounding said neck portion.

17. A bone implant according to claim 16, wherein said bone implant additionally includes:
    a projection provided on at least one of said cap portion and said neck portion; and
    a recess provided on the other of said cap portion and said neck portion;
    said projection and said recess being dimensioned to releasably engage one another when said cap portion substantially surrounds said neck portion.

18. A bone implant according to claim 11, wherein:
    said cover element comprises at least one of a non-resorbable plastic, a silicone, a metal, and titanium.

19. A bone implant according to claim 11, wherein said cover element includes perforations extending therethrough.

20. A bone implant according to claim 11, wherein said cover element is substantially deformable.

* * * * *